United States Patent [19]
Dembinski et al.

[11] Patent Number: 4,658,017
[45] Date of Patent: Apr. 14, 1987

[54] METHOD FOR THE LARGE SCALE PURIFICATION OF HUMAN FIBROBLAST INTERFERON

[75] Inventors: Wlodzimierz E. Dembinski; Eugene Sulkowski, both of Buffalo, N.Y.

[73] Assignee: Health Research, Inc. (Roswell Park Division), Buffalo, N.Y.

[21] Appl. No.: 579,994

[22] Filed: Feb. 14, 1984

[51] Int. Cl.$^4$ .............................. C07K 3/20; C07K 15; C07K 26; A61K 45/02
[52] U.S. Cl. ..................................... 530/351; 424/85; 435/811
[58] Field of Search ...... 424/85; 260/112 R, 112.5 R; 435/68, 811; 530/351

[56] References Cited

U.S. PATENT DOCUMENTS

| | | | |
|---|---|---|---|
| 4,172,071 | 10/1979 | De Maeyer et al. | 424/85 |
| 4,257,938 | 3/1981 | Hosoi et al. | 424/85 |
| 4,278,661 | 7/1981 | Knight, Jr. | 424/85 |
| 4,289,689 | 9/1981 | Friesen et al. | 424/85 |
| 4,296,025 | 10/1981 | Sugimoto | 424/85 |

OTHER PUBLICATIONS

Steward II, *The Interferon System*, Springer-Verlag, Wien New York, pp. 168-171, (1979).
Sulkowski, *Texas Reports on Biology and Medicine*, vol. 41, pp. 234-239, (1981-1982).
Berg et al., *Interferon and Interferon Inducers*, Marcel Dekker Inc., New York and Basel, pp. 34-38, (1980).
Davey et al., Biochemistry, vol. 15, pp. 704-713, (1976).
Whitman et al., Annals of the New York Academy of Sciences, vol. 350, p. 559, (1980).
Mikulski et al., Preparative Biochemistry, vol. 10, pp. 103-119, (1980).
Leong et al., Methods in Enzymology, vol. 78, pp. 87-101, (1981).
Milulski et al., Int. Sci. Mem., Oct., I-A335/1, (1976).
Knight, E., Jr. J. Biol. Chem., vol. 250, pp. 4139-4144, (1975).
Knight, E., Jr. Proc. Natl. Acad. Sci. U.S.A., vol. 73, pp. 520-523, (1976).
Tan, Y. S., Methods in Enzymology, vol. 78, Academic Press, New York, London, Toronto, Sydney, San Francisco, pp. 422-430.
Friesen et al., Archives of Biochemistry and Biophysics, vol. 206, No. 2, Feb., pp. 432-450, (1981).
Smith-Johannsen et al., Journal of Interferon Research, vol. 3, No. 4, pp. 473-477, (1983).
Jankowski et al., Journal of Virology, vol. 16, No. 5, pp. 1124-1130, (Nov. 1975).
Heine et al., Annals New York Academy of Sciences, vol. 350, pp. 364-373, (1980).
Heine et al., Methods in Enzymology, vol. 78, pp. 448-457, (1981).

*Primary Examiner*—Blondel Hazel
*Attorney, Agent, or Firm*—Christel, Bean & Linihan

[57] ABSTRACT

A process for the large scale purification of human fibroblast interferon produced by human diploid fibroblasts under superinduction conditions characterized by a sequence of four chromatographic steps namely:
 (1) separation on CM-agarose;
 (2) separation on ConA-agarose;
 (3) separation on phenyl-agarose; and
 (4) elimination of ethylene glycol using CM-agarose which process yields a final overall recovery not less than 60% of the crude interferon starting material and having a specific activity not less than $1 \times 10^8$ units per mg of protein.

4 Claims, No Drawings

METHOD FOR THE LARGE SCALE PURIFICATION OF HUMAN FIBROBLAST INTERFERON

BACKGROUND OF THE INVENTION

The present invention relates to a method for the purification of fibroblast interferon. More particularly, the present invention is directed to a large scale purification procedure for human fibroblast interferon (HuIFN-$\beta$) produced by human diploid fibroblasts under superinduction conditions.

DESCRIPTION OF THE PRIOR ART

Several years of work on the purification and characterization of fibroblast interferons have demonstrated that these interferons, under appropriate solvent conditions can be purified on a wide variety of matrices (Concanavalin A-agarose, phenylagarose, octyl-agarose, poly-V-agarose, blue-agarose, serum albumin agarose, controlled pore glass chromatography, metal chelate chromatography, dye chromatography, etc.). This subject has been extensively reviewed in recent years by W. E. Steward II, "The Interferon System", Springer-Verlag, Wien New York, 1979, pages 168–171, E. Sulkowski (1981–1982) *Texas Reports on Biology and Medicine,* vol. 41, pages 234–239, K. Berg and I. Heron, "Interferon and Interferon Inducers", Marcel Dekker Inc., New York and Basel, 1980, pages 34–38.

Concanavalin A-agarose (ConA-agarose) has been used for the purification of human fibroblast interferon since 1976 [Davey et al. (1976) Biochemistry 15, 704–713]. In 1981, H. J. Friesen and S. Pestka were granted U.S. Pat. No. 4,289,689 for ConA-Sepharose as a part of the preparation of homogenous human fibroblast interferon. However, the recoveries reported from different laboratories varied substantially: 15% —H. J. Friesen and S. Pestka, U.S. Pat. No. 4,289,689; 10%–14% —J. E. Whitman et al. (1980) Annals of the New York Academy of Sciences 350, 599; 60%—A. Mikulski et al. (1980) Preparative Biochemistry 10, 103–119; 60%—S. S. Leong and J. S. Horoszewicz, Methods in Enzymology vol. 78, pp 87–101 (1981). The general principles and methodologies regarding ConA-Sepharose purification of interferon described by these authors are virtually the same Phenyl-agarose has been employed for the purification of human fibroblast interferon since 1967 [Mikulski, A. J., Horoszewicz, J. S., Sulkowski, E., and Carter, W. A. (1967) Int. Sci. Mem., October, I-A335/1]. This ligand provides for modest purification of human fibroblast interferon, but when used after interferon chromatography on ConA-agarose also concentrates the interferon and eliminates the traces of leaking lectin (concanavation A).

A cation exchanger, carboxymethyl-Sephadex, has been used in a combined process of: acid-ammonium sulfate precipitation, gel filtration, ion exchange chromatography and SDS polyacrylamide gel electrophoresis by E. Knight to purify mouse fibroblast interferon [Knight, E., Jr. (1975), J. Biol. Chem. 250, 4139–4144] and later to purify human fibroblast interferon [Knight, E., Jr. (1976), Proc. Natl. Acad. Sci. U.S.A. 73, 520–523]. Also CM-cellulose has been used in a procedure for purification of human fibroblast interferon to shift acidic pH of the interferon preparation eluted from controlled pore glass column, to neutral one without causing precipitation before it could be applied to the immunoabsorbent column [Tan, Y. H., Methods in Enzymology vol. 78, Academic Press, New York, London, Toronto, Sydney, San Francisco, 1981, pages 422–430].

BRIEF SUMMARY OF THE INVENTION The present invention provides a process for the purification of human fibroblast interferon produced by human diploid fibroblasts under superinduction conditions which process produces a purified fibroblast interferon end product having a final recovery not less than 60% of the starting material, and a specific activity not less than $1 \times 10^8$ units/mg protein, comprising the following steps carried out in the sequence specified:

(a) contacting an aqueous solution of human fibroblast interferon which has been first mildly acidified by the addition of a suitable buffering agent, with a weakly acidic cation exchange medium, preferably carboxymethyl (CM) agarose to adsorb the interferon on the medium;

(b) eluting the interferon adsorbed on the medium of step (a) by washing the medium with a suitable acidic or basic eluting solution containing a suitable salt such as potassium or sodium chloride to obtain a solution of purified interferon having an activity not less than 95% of the starting material and having a protein content of not more than 5% of the starting material;

(c) subjecting the solution of purified interferon obtained in step (b) to affinity chromatography on a suitable lectin exchange material, preferably ConA-agarose, to adsorb the interferon on the exchange material;

(d) developing the exchange material with an eluant comprising methyl-$\alpha$-D-Mannopyranoside and thereafter incubating the exchange material for a sufficient length of time in the presence of said methyl-$\alpha$-D-mannopyranoside;

(e) eluting the exchange material of step (d) with a suitable amount of ethylene glycol to obtain an eluate containing ethylene glycol and the purified interferon in which the final concentration of the ethylene glycol is not more than 50% (vol/vol), and preferably not more than 40% (vol/vol);

(f) subjecting the eluate obtained in step (e) to chromatography on a hydrophobic sorbent medium, preferably Phenyl-agarose to absorb the interferon on the sorbent medium;

(g) eluting the interferon adsorbed in step (f) with a suitable eluant comprising preferably 75% (vol/vol) ethylene glycol in 0.02 M sodium phosphate, 0.15 M sodium chloride, pH 7.4 (PBS), and (h) subjecting the eluate obtained from step (g) which has been first mildly acidified by the addition of a suitable buffering agent to chromatography on a weakly acidic cation exchange medium, preferably carboxymethyl (CM) agarose, to eliminate the ethylene glycol and endotoxins and to concentrate the interferon to the desired strength.

The purification process according to the present invention consists of a sequence of four chromatographic steps as follows: (1) CM-agarose; (2) ConA-agarose; (3) Phenyl-agarose and (4) CM-agarose.

The initial treatment of the crude interferon with CM-agarose is believed to be critical to the overall success of the present purification procedure. As stated previously herein, steps 2 and 3 of this process have been used in combination by other researchers in an attempt to obtain an efficient and economical method for purifying interferon. However, this two-step process produced varying yields of interferon and the reported results were not consistently reproducible.

Recovery after the separation of biological molecules by column chromatography is rarely 100%. The addition of extra purification steps, while increasing purity, usually decreases overall recovery. One would not expect human fibroblast interferon recovery to be significantly enhanced by the addition of a third step, a preliminary CM-agarose separation step, to the prior known two-step procedure.

Experiments have shown that in the crude interferon solution there are some components which have the same or higher affinity towards the ConA lectin column than do the interferon molecules so that, when the interferon absorbed on the column is replaced by these components there is an apparent decrease in the capacity of lectin towards the interferon solution. In addition other substances are believed to be present in the original interferon solution which may interfere with the desorption of interferon from the lectin column. Such theories would tend to explain the importance of the sequence employed (i.e. using CM-agarose as the first, not the third step of the process).

The primary function of the ConA-agarose step is the purification of interferon based on its glycoprotein nature. In prior procedures, the ConA column was often discarded after a single use. However, it has now been found that when ConA-agarose is used after the initial CM-agarose step, the ConA-agarose may be utilized several (10–20) times.

The incubation of the lectin column in the presence of 0.1 M methyl-$\alpha$-D-mannopyranoside ($\alpha$-MM) is believed to be critical to obtaining better yields of interferon. In all published procedures known to date, the interferon is washed with 0.1 M $\alpha$-MM and immediately eluted with 0.1 M $\alpha$-MM in 50% ethylene glycol. In our improved procedure the interferon is washed and subsequently incubated for several hours with the $\alpha$-MM. Optimally the incubation time will be 12–48 hours, but shorter or longer incubation periods are within the scope of the instant invention.

The Phenyl-agarose step functions to concentrate the interferon and provides additional, though modest, purification. In addition this step eliminates traces of leaking lectin (Concanavalin A).

The fourth step is a repetition of the cation-exchange operation performed in the initial process step. This treatment does not primarily serve a purification purpose, but rather it serves to effectively eliminate the ethylene glycol more efficiently than dialysis, concentrate the interferon so that high titers can be achieved in the eluants and remove endotoxins which may be acquired during the previous purification steps.

The use of CM-agarose and other process modifications introduced by the procedure practiced according to the instant invention are believed to be responsible for producing an unexpectedly high overall yield of purified human fibroblast interferon. The initial purification using CM-agarose gives approximately 50-fold purification with virtually complete recovery of interferon. Moreover, pyrogens, which may originate during the preparation of crude material, are found in the "breakthrough" fraction and thus are eliminated. In addition, as a result of the improved process, the amount of ConA-agarose needed to carry out the purification process, the elution time and the time required for loading the interferon on the Phenyl-agarose have all been reduced about five fold, thereby making the process more beneficial in terms of efficiency and economy, and making it more suitable for large scale use.

DETAILED DESCRIPTION OF THE INVENTION

Preferred Preparation of Materials

A. Sorbents

1. General Guidelines
   (a) All sorbents should be prepared under semi-sterile conditions.
   (b) All columns should be prepared and equilibrated at 4° C.
2. CM-agarose (1)
   (a) Mix 0.4L of CM-agarose, available commercially as CM-Sepharose CL-6B cake (Pharmacia) with 0.4L of sodium acetate, 2 M, pH 4.9.
   (b) Decant supernatant and equilibrate CM-Sepharose with 0.5L of 0.1 M sodium acetate (pH 5.0).
   (c) Decant supernatant. Add CM-Sepharose CL-6B to crude interferon (adjusted to pH 5.0).
3. ConA-agarose
   (a) Pack K-25/40 (Pharmacia) column (2.5 × 8.0 cm) with 40 ml of ConA-agarose, available commercially as ConA-Sepharose 4B (Pharmacia).
   (b) Wash column overnight with 0.6L of PBS.
4. Phenyl-agarose
   (a) Pack a K-25/40 (Pharmacia) column (2.5 × 10 cm) with 50 ml of Phenyl-agarose, available commercially as Phenyl-Sepharose CL-4B (Pharmacia).
   (b) Wash column overnight with 1.5L of 40% (vol/vol) ethylene glycol (EG) containing PBS.
5. CM-agarose (2)
   (a) Pack a K-16/20 (Pharmacia) column (1.6 × 5.0 cm) with 10 ml of the CM-Sepharose CL-6B (Pharmacia) cake.
   (b) Wash the column with 10 bed volumes (100 ml) of 38% (vol/vol) ethylene glycol containing sodium acetate, 0.1 M, pH 4.5.

B. Other

1. After each purification cycle, disassemble, wash and rinse the column with tap water, then double distilled water, and air dry.
2. Wash and rinse all inner sides of tubing with tap water followed by double distilled water, 70% ethanol and air dry.
3. One hour before using, rinse columns and all tubing with 70% ethanol.
4. Drain 70% ethanol.
5. Wash column with sterile double distilled water.
6. Wash column with starting buffer.

BEST MODE CONTEMPLATED FOR CARRYING OUT THE PURIFICATION PROCEDURE

The first cation exchange step can be performed batchwise in order to reduce the adsorption time. The remainder of the procedure is preferably done on columns.

A. CM-agarose

1. Pool 8L of crude, pelliconized interferon into a sterile reservoir in a biocontainment hood or sterile room.

2. Add 0.4L of sodium acetate, 2 M, pH 4.9.

3. Transfer 8.4L of crude (pH 5.0) into two 3029 Falcon roller bottles (Falcon).

4. Add 0.2L of CM-agarose to each bottle.

5. Place the roller bottles on a cell production roller apparatus (Bellco Glass), set at speed "5 high" for 1 hour, at 4° C.

6. Collect contents of both bottles on a Buchner fritted coarse disc funnel under slight vacuum in a biocontainment hood.

7. Wash cake in succession with approximately 1L of sodium acetate 0.1 M, pH 5.0 and then with 1L of sodium acetate, 0.01M, pH 5.0, and then transfer cake in 0.01 M, pH 5.0 sodium acetate buffer to a K-50/30 column.

8. Drain sodium acetate from the column bed such that buffer level is just above surface of the cake.

9. Connect the ConA-agarose column to the CM-agarose column and apply 2L of sodium phosphate, pH 8.0 containing 1 M NaCL at a flow rate 10 ml/cm$^2$/hr [0.2L/hr].

B. ConA-agarose

1. Apply eluant from CM-agarose on a ConA-agarose column at a flow rate of 40 ml/cm$^2$/hr.

2. Rinse column with 0.2L of PBS (flow rate 0.25L/hr).

3. Develop column with 0.25L of 0.1 M α-MM in PBS (flow rate 0.25L/hr).

4. Wash column with 0.4L of PBS.

5. Apply next portion of eluant from CM-agarose (as in points 1 and 2).

6. Develop column with 0.1L of 0.1 M α-MM in PBS (flow rate 0.25L/hr).

7. Stop column (in presence of 0.1 M α-MM in PBS) for 2 days.

8. Desorb proteins bound to ConA-agarose with 0.2L of eluant comprising ethylene glycol, 0.1 M α-MM and PBS having a final ethylene glycol concentration of 50% (vol/vol) at a flow rate of 10 ml/cm$^2$/hr (50 ml/hr).

9. Collect eluate into plastic bottle containing 50 ml of PBS and 250 mg of human serum albumin, so that the final concentration of ethylene glycol in 40%.

10. Take two 1 ml samples for routine sterility and pyrogen tests, and titration; freeze eluant at −80° C.

C. Phenyl-agarose

1. Thaw, at +40° C., the eluants containing the interferon, collected from ConA-agarose and pool.

2. Apply the pooled eluants on a K-2.5/40 column at a flow rate of 30 ml/cm$^2$/hr (0.15L/hr).

3. Wash the column with 300 ml of ethylene glycol, 40% (vol/vol) in PBS (flow rate 0.15L/hr).

4. Displace interferon from the column with 300 ml of ethylene glycol, 75% (vol/vol) in PBS, pH 7.4 containing human serum albumin (0.1 mg/ml) into a plastic bottle with 260 ml of PBS so that the final concentration of ethylene glycol is 40%.

D. CM-agarose (2)

1. To approximately 550 ml of the material from the previous step, add approximately 28 ml of sodium acetate, 2 M, pH 4.4.

2. Charge material on a K-16/20 column containing 10 ml CM-agarose, at a flow rate of 20 ml/cm$^2$/hr.

3. Wash the column with 100 ml of sodium acetate, 0.1 M, pH 4.5 (flow rate 50 ml/hr).

4. Wash the column with 50 ml of monobasic sodium phosphate (NaH$_2$PO$_4$), 0.02 M, pH 4.7 (flow rate 50 ml/hr).

5. Desorb interferon from the column with approximately 100 ml sodium chloride 0.75 M in PBS pH 7.4 at a flow rate of 15 ml/cm$^2$/hr (30 ml/hr). The volume of 0.75 M NaCl in PBS, pH 7.4, used for desorption of interferon depends on the expected titer and the desired volume per vial.

6. Dilute eluate from column 5-fold with PBS, pH 7.4.

7. Add human serum albumin to a final concentration of 1 mg/ml.

The active ligand components of the chromatographic separation materials used in carrying out the present process can be immobilized on any one of several commonly used support matrices. Agarose was used in all of the Examples set forth herein as it was readily available commercially from Pharmacia, Inc. However, other commercially available separation mediums utilizing different support structures may be employed and are considered to be within the scope of the present process.

It is recommended that this process be carried out at a temperature of about 4° C. in order to slow down bacterial growth and to impede enzyme activity in the event enzymes are present in the starting material. However, temperature is not critical and this process may be carried out over a wide range of temperatures including room temperature.

In step (a) of the procedure (page 3 of the specification), it is preferred that the weakly acidic cation exchange medium be buffered to a pH of about 5 for optimum results. However, the actual pH used may range from 4–6 without having any significant detrimental effect on the final interferon recovery obtained.

In step (b) of the instant process (page 3 of the specification), the eluting solvent may have a pH in the range of 5–9. However, in order to minimize damage to the ConA-agarose medium, a pH of about 8.0 was determined to be preferable.

The following examples are included for illustrative purposes only and are not intended to limit the scope of this invention. All interferon titers are expressed in terms of reference units per ml or units per mg against a reference standard for human fibroblast interferon (GO23-902-527) provided by the National Institutes of Health as determined by known standard assay procedures.

EXAMPLE 1

8L of crude pelicorized human fibroblast interferon (60,000 units/ml, 2 mg protein/ml) were mixed with 0.4L of sodium acetate, 2 M, pH 4.9 and this mixture was transferred into two roller bottles. To each bottle 0.2L of CM-Sepharose CL-6B were added and the bottles were placed on a cell production apparatus (Belco glass) set at a speed of "5 high" for 1 hour, at 4° C. The contents of both bottles were collected in a Buchner fritted disc funnel under slight vacuum. The cake was washed with approximately 1L of sodium acetate, 0.1 M, pH 5.0 and then washed with approximately 1L of sodium acetate 0.01M, pH 5.0 and transferred in it into a K-50/30 (Pharmacia) column. After removing excessive acetate buffer the column was eluted with 1.5L of phosphate buffer, 0.02 M, pH 8.0 containing 1 M NaCl. $4.7 \times 10^8$ interferon units, and 150 mg of protein were recovered. (This represents a 98% recovery of interferon activity and a 99% removal of protein from the starting material.

EXAMPLE 2

A CM-Sepharose CL-6B column was loaded with interferon as in Example 1. In this Example the starting crude material contained $4.3 \times 10^8$ interferon units and 16 g. protein. The column was connected with 40 ml of ConA-Sepharose 4B packed in a K-25/40 (Pharmacia) column. The CM-Sepharose CL-6B was eluted overnight with 1.5L of phosphate buffer, 0.02 M, pH 8.0 containing 1 M sodium chloride. After loading, the columns were disconnected and ConA-Sepharose 4B was washed with the following solutions:

(1) 0.2L of sodium phosphate buffer 0.02 M mixed with 0.15 M sodium chloride (PBS),
(2) 0.25L of 0.1 M α-MM in PBS,
(3) 0.4L of PBS, and again loaded with interferon eluted from the CM-Sepharose CL-6B column ($4.8 \times 10^8$ interferon units, 16 g. protein in starting material). After charging, the columns were disconnected and the ConA-Sepharose 4B was washed with
(1) 0.2L of PBS,
(2) 0.15L of 0.1 M α-MM in PBS and incubated for two days.

The proteins bound to ConA-Sepharose 4B were desorbed with 0.2L of eluant having a final concentration of 50% (vol/vol) ethylene glycol, 0.1 M α-MM and PBS. The eluate was collected into a plastic bottle containing 50 ml of PBS. $7.7 \times 10^8$ interferon units (85% recovery of the starting material) and 5.1 mg of protein were recovered. 250 mg of human serum albumin were then added to eluate. The specific activity of the interferon recovered from the ConA-agarose was $1.5 \times 10^8$ interferon units/mg protein.

EXAMPLE 3

The $2.5 \times 10^5$ interferon units collected and pooled after the ConA-Sepharose 4B chromatography were applied to a K-25/40 (Pharmacia) column, loaded with 50 ml of Phenyl-Sepharose CL-4B, equilibrated with 40% (vol/vol) ethylene glycol in PBS and washed with 300 ml of 40% (vol/vol) ethylene glycol in PBS and then eluted with 300 ml of 75% (vol/vol) ethylene glycol in PBS. The eluate was collected in a plastic bottle containing 260 ml of PBS. The final concentration of the ethylene glycol present in the eluate (560 ml) was 40% (vol/vol). ($2.5 \times 10^9$ interferon units and 14 mg of protein were recovered.) This represents a 100% recovery of the starting material which had been collected and pooled at the start of the Example. The specific activity of the interferon recovered was $1.8 \times 10^8$ interferon units/mg protein.

EXAMPLE 4

Approximately 2.8 ml of sodium acetate, 2 M, pH 4.4 were added to the 2.5 interferon units recovered in Example 3 which were contained in 560 ml of 40% (vol/vol) solution of ethylene glycol after chromatography on Phenyl-agarose. This material was then charged on K-16/20 (Pharmacia) column containing 10 ml of CM-Sepharose CL-6B, equilibrated with solution containing ethylene glycol 38% (vol/vol), sodium acetate, 0.1 M pH 4.4. After charging the column was washed with 100 ml of sodium acetate 0.1 M, pH 4.5 and with 50 ml of monobasic sodium phosphate, 0.02 M, pH 4.7. The interferon was desorbed from the column with 100 ml sodium chloride 0.75 M, in sodium phosphate, 0.02 M, pH 7.4. The eluate was collected into a plastic bottle containing 400 ml of sodium phosphate, 0.02 M, pH 7.4 so the concentration of the sodium chloride was 0.15 M. ($2.3 \times 10^9$ inferferon units and 11.5 mg protein were recovered.) The interferon recovery from this experiment was 92%, and the specific activity was $2 \times 10^8$ interferon units/mg protein.

It is to be understood that various changes and details, materials and steps, which have been herein described in order to explain the nature of this invention, may be made by those skilled in the art within the principles and scope of this invention. Accordingly, the present invention is not to be confined to the details set forth and this application is intended to cover such modifications or changes as may come within the scope of the following claims.

We claim:

1. A process for the large scale purification of human fibroblast interferon produced by human diploid fibroblasts under superinduction conditions which process produces a purified fibroblast interferon end product having a final recovery not less than 60% of the starting material, and a specific activity not less than $1 \times 10^8$ units/mg protein, comprising the following steps carried out in the sequence specified:

(a) contacting an aqueous solution of human fibroblast interferon which has been first mildly acidified by the addition of a suitable buffering agent, with a weakly acidic cation exchange medium having one or more carboxymethyl functional groups as the active ligand component of said medium to absorb the inferferon on said medium;

(b) eluting the interferon absorbed on the medium of step (a) by washing the medium with a suitable acidic or basic eluting solution containing a suitable salt such as potassium or sodium chloride to obtain a solution of purified interferon having an activity not less than 95% of the starting material;

(c) subjecting the solution of purified interferon obtained in step (b) to affinity chromatography on a suitable exchange material wherein lectin, preferably concanavalin A, is the active ligand component of said material, to adsorb the interferon on said exchange material;

(d) developing said exchange material with an eluant comprising methyl-α-D-mannopyranoside and thereafter incubating said exchange material for a sufficient length of time in the presence of said methyl-α-D-mannopyranoside;

(e) eluting the exchange material of step (d) with a suitable amount of ethylene glycol to obtain an eluate containing ethylene glycol and the purified interferon in which the final concentration of the ethylene glycol is not more than 50% (vol/vol), and preferably not more than 40% (vol/vol);

(f) subjecting the eluate obtained in step (e) to chromatography on a hydrophobic sorbent medium having one or more phenyl functional groups as the active ligand component of said sorbent medium to absorb the interferon on said sorbent medium;

(g) eluting the interferon adsorbed in step (f) with a suitable eluant comprising preferably 75% (vol/vol) ethylene glycol in 0.02 M sodium phosphate, 0.15 M sodium chloride, pH 7.4 (PBS); and (h) subjecting the eluate obtained from step (g), which has been first mildly acidified by the addition of a suitable buffering agent, to chromatography on a weakly acidic cation exchange medium having one or more carboxymethyl functional groups as the active ligand component of said medium to eliminate the ethylene glycol and endotoxins and to concentrate the interferon to the desired strength.

2. The process according to claim 1 wherein the weakly acidic cation exchange medium of step (a) is carboxymethyl agarose; the lectin exchange material of step (c) is ConA-agarose; the hydrophobic sorbent medium of step (f) is phenyl-agarose and the weakly acidic cation exchange medium of step (h) is carboxymethyl agarose.

3. The process according to claim 2 wherein the lectin exchange material of step (c) is incubated in the presence of said methyl-α-D-mannopyranoside for 3–48 hours.

4. A process for the large scale purification of human fibroblast interferon produced by human diploid fibroblast under super-induction conditions which process produces a purified fibroblast interferon end product having a final recovery of not less than 60% of the starting material and a specific activity not less than $1 \times 10^8$ units per mg protein comprising a sequence of four chromatographic steps performed in the following sequential order:

(a) chromatography on CM-agarose,
(b) chromatography on ConA-agarose,
(c) chromatography on phenyl-agarose and
(d) chromatography on CM-agarose.

* * * * *